US00PP31300P2

(12) United States Plant Patent
van Nijnatten

(10) Patent No.: US PP31,300 P2
(45) Date of Patent: Dec. 31, 2019

(54) ***SYRINGA* PLANT NAMED 'ANNYS200809'**

(50) Latin Name: *Syringa hybrida*
Varietal Denomination: Annys200809

(71) Applicant: André van Nijnatten, Zundert (NL)

(72) Inventor: André van Nijnatten, Zundert (NL)

( * ) Notice: Subject to any disclaimer, the term of this patent is extended or adjusted under 35 U.S.C. 154(b) by 0 days.

(21) Appl. No.: 15/932,628

(22) Filed: Mar. 28, 2018

(51) Int. Cl.
*A01H 5/02* (2018.01)

(52) U.S. Cl.
USPC ..... Plt./248

(58) Field of Classification Search
USPC ..... Plt./248
CPC ..... A01H 5/02; A01H 6/00
See application file for complete search history.

*Primary Examiner* — Keith O. Robinson
(74) *Attorney, Agent, or Firm* — Penny J. Aguirre

(57) ABSTRACT

A new cultivar of *Syringa hybrida* plant named 'Annys200809' that is characterized by its compact plant habit and dwarf plant size, its flower panicles that are large in size, its sweet flower fragrance, its flowers that are red-purple with white petal lobes opening from red-purple flower buds, and its free flowering habit.

2 Drawing Sheets

Botanical classification: *Syringa hybrida.*
Variety denomination: 'Annys200809'.

CROSS REFERENCE TO A RELATED APPLICATION

This application is related to a European plant breeders' rights application filed on Oct. 16, 2013, application No. 2013/2647. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Syringa* of hybrid origin that is botanically known as *Syringa* 'Annys200809' and will be referred to hereafter by its cultivar name, 'Annys200809'. 'Annys200809' is a new cultivar of lilac grown for use as an ornamental landscape plant.

'Annys200809' originated as a seedling that arose from seed planted from open pollination of Syringa 'Pink Perfume' (U.S. Plant Pat. No. 24,252) in Zundert, The Netherlands in July of 2008. The male parent is therefore unknown.

Asexual propagation of the new cultivar was first accomplished by grafting in 2010 under the direction of the Inventor in Zundert, The Netherlands. Asexual propagation by grafting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Annys200809' as a unique cultivar of *Syringa.*

1. 'Annys200809' exhibits a compact plant habit and dwarf plant size.

2. 'Annys200809' exhibits flower panicles that are large in size.
3. 'Annys200809' exhibits a sweet flower fragrance.
4. 'Annys200809' exhibits repeat blooming habit; blooming in summer with a second flush in autumn.
5. 'Annys200809' exhibits flowers that are red-purple with white petal lobes opening from red-purple flower buds.
6. 'Annys200809' exhibits free flowering habit.

The female parent of 'Annys200809', 'Pink Perfume', is similar to 'Annys200809' in having a compact plant habit and fragrant flowers. 'Pink Perfume' differs from 'Annys200809' in having fewer leaflets per branch, flower buds that are grey-purple in color and flower petals that are red-purple in color (lack white lobes) when fully open. The new *Syringa* can also be compared to *Syringa* cultivar 'Penda' (U.S. Plant Pat. No. 20,575) and *Syringa meyeri* 'Palabin' (not patented). 'Penda' is similar to 'Annys200809' in having a compact plant habit, fragrant flowers, and a re-blooming habit. 'Penda' differs from 'Annys200809' in having leaves that are smaller in size and in having a more spreading plant habit. 'Palabin' is similar to 'Annys200809' in having a compact and dense plant habit. 'Palabin' differs in having flowers that are pale pink in color and in having a broader plant habit.

BRIEF DESCRIPTION OF THE DRAWINGS

The accompanying colored photographs illustrate the overall appearance and distinct characteristics of the new *Syringa*. The photographs were taken of a 7-month-old plant as grown outdoors in 3-Liter containers in Zundert, The Netherlands.

The photograph in FIG. 1 provides a side view of a plant of 'Annys200809' in bloom.

Figure 1:
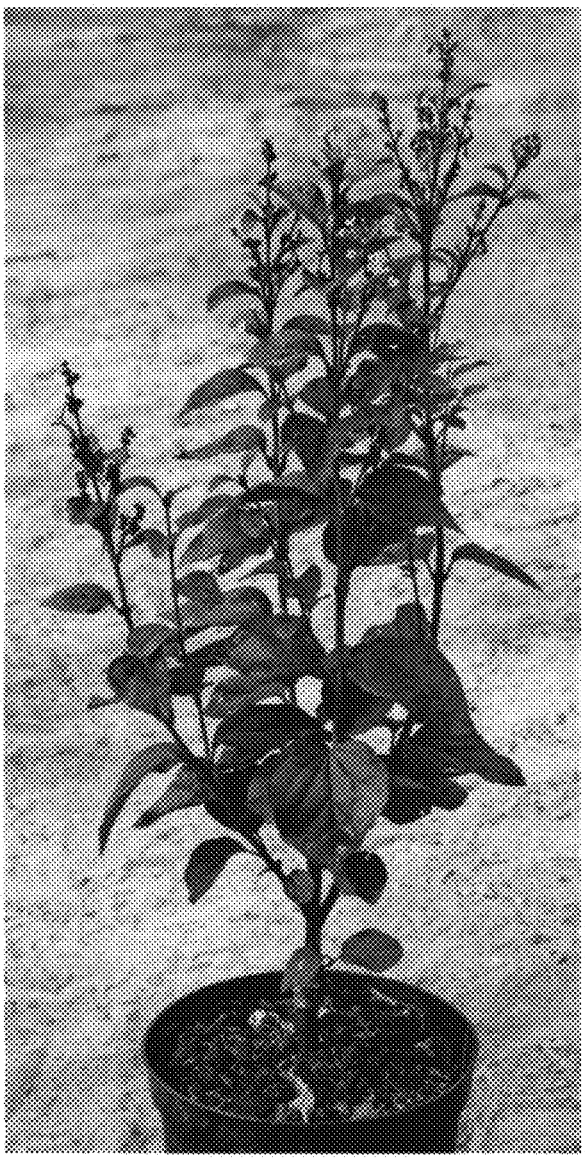
Figure 2:
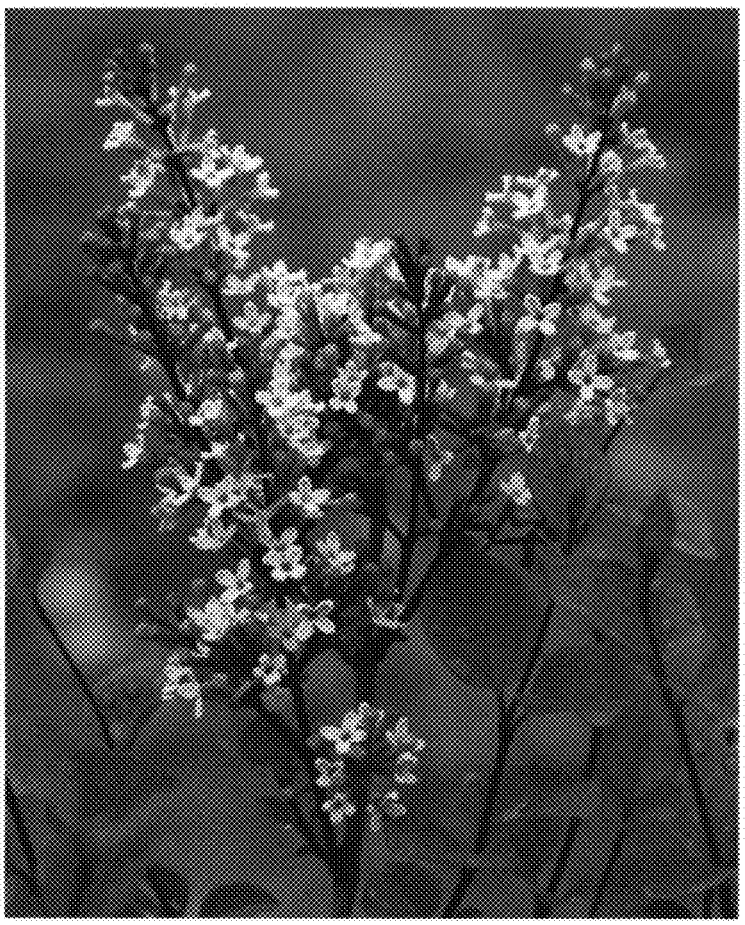

The photograph in FIG. 2 provides a close-up view of the inflorescences of 'Annys200809'.

Figure 3:
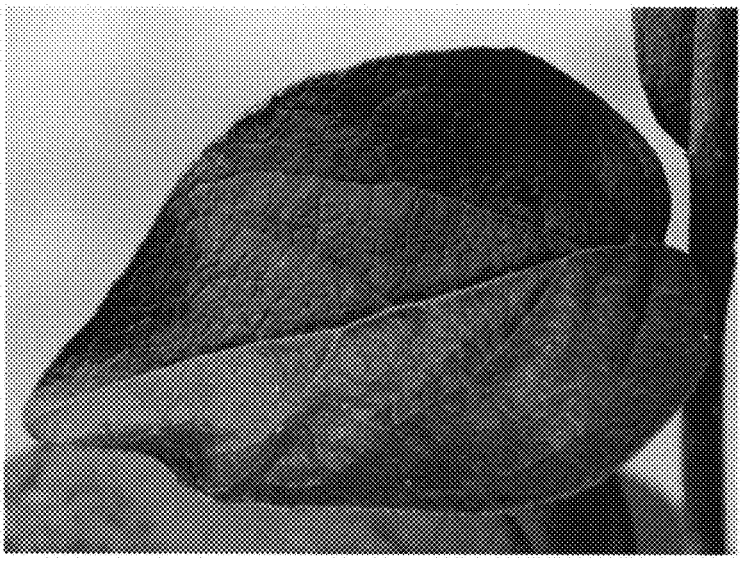

The photograph in FIG. 3 provides a close-up view of a leaf of 'Annys200809'.

The colors in the photographs are as close as possible with the photographic and printing technology utilized and the color values cited in the detailed botanical description accurately describe the colors of the new *Syringa*.

DETAILED BOTANICAL DESCRIPTION

The following is a description of 7-month-old plants as grown outdoors in 3-liter containers in Zundert, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—August and May in The Netherlands.

*Plant type.*—Deciduous shrub.

*Plant habit.*—Broad upright and ovate.

*Height and spread.*—An average of 56.5 cm in height and 26 cm in width, obtains an average of 1.25 m in height and 60 cm in width in the landscape.

*Hardiness.*—U.S.D.A. Zones 2 to 9.

*Diseases.*—No resistance or susceptibility to diseases has been observed.

*Root description.*—Fibrous and dense, a blend of 165A and 161D in color.

*Propagation.*—Grafting onto rootstock.

*Growth rate.*—Moderate.

*Root development.*—Cuttings from grafting taken in summer root in 4 to 6 weeks, are hardened in winter and plugs are potted into P9 containers in spring.

Branch description:

*Branch shape.*—Rounded.

*Branch color.*—Young; 148A, flushed with 183A, older branches; 199B.

*Branch size.*—Lateral branches; an average of 37.2 cm in length and 3 mm in diameter.

*Branch surface.*—Older stems; smooth, young stems covered with soft pubescent hairs an average of 0.5 mm in length and N155A in color.

*Branch quantity.*—Average of 4 main branches, average of 5 lateral branches per main branch, average of 20 lateral branches per plant.

*Internode length.*—Up to 4.1 cm.

*Branching.*—Freely branching, upright.

Foliage description:

*Leaf shape.*—Ovate to broad ovate.

*Leaf division.*—Simple.

*Leaf base.*—Obtuse to short attenuate.

*Leaf apex.*—Bluntly acute.

*Leaf fragrance.*—None.

*Leaf venation.*—Pinnate, upper surface color; 144A, lower surface color; 144B.

*Leaf margins.*—Entire and slightly undulate, densely covered with pubescent hairs 0.5 mm in length and color ranges between matching margin color and N155A.

*Leaf arrangement.*—Opposite.

*Leaf attachment.*—Petiolate.

*Leaf surface.*—Both surfaces are slightly leathery, upper surface is glabrous and lower surface is sparsely pubescent with short hairs an average of 0.5 mm in length and N155A in color.

*Leaf size.*—An average of 5.3 cm in length and 3.9 cm in width.

*Leaf quantity.*—An average of 18 leaves (9 pairs) per lateral branch.

*Leaf color.*—Young leaf upper surface 146A, flushed with 183A especially at the margins, young lower surface; 146B to 148B, mature upper surface; color between N137A and 147A, mature lower surface; 147B.

*Petioles.*—An average of 1.1 cm in length and 1.5 mm in width, both surfaces glabrous and slightly glossy, 144A and flushed with 183A in color.

Inflorescence description:

*Inflorescence type.*—Thyrse compound panicles on terminals and laterals, narrow ovate in overall shape.

*Inflorescence size.*—An average of 11 cm (including peduncle) in height and 5.3 cm in width.

*Flower buds.*—Spathulate in shape, an average of 1.1 cm in length and 2.5 mm diameter, color; 72B, tube 77B.

*Flower fragrance.*—Sweet, strong.

*Persistence of flowers.*—Self-cleaning.

*Lastingness of flowers.*—Individual panicles last an average of 10 days.

*Flower quantity.*—An average of 135 flowers per lateral stem, average of 7,500 flowers and buds per plant.

*Flower type.*—Salverform, single.

*Flower aspect.*—Upright and slightly outward.

*Flower size.*—An average of 7.5 mm in diameter, 1.1 cm in depth.

*Petals.*—4, salverform, corolla 4-lobed, an average of 1.3 cm in length and 2 mm in width, narrow oblanceolate in shape, acute apex, margins of corolla lobes entire with undulation absent and moderately involute, aspect of corolla lobes is horizontal to semi-erect, lower 77% fused into tube, upper and lower surfaces smooth and matte, color; when opening and fully open upper surface 75A to 75B, free lobes NN155C, tube 75A, when opening and fully open lower surface 75A.

*Sepals.*—4, rotate, fused into a campanulate shape, entire margins, broad acute apex, 1.5 mm in length, 1 mm in width, color; immature and mature upper and lower surface 183D and tinged with 153C.

*Calyx.*—Rotate, average of 1.5 mm in length and diameter.

*Peduncles.*—Primary; an average of 10 cm in length and 1.5 mm in width, held upright, axillary; held at an average angle of 30°, an average of 1.8 cm in length and 1.3 mm in width, primary and axillary; moderate strength, 200A to 200B in color, surface is matte to slightly glossy, sparsely covered with pubescent hairs an average of 0.5 mm in length and a color between N155A and surface color.

*Pedicels.*—None, sessile to peduncle.

Reproductive organs:

*Pistils.*—1, average of 2.5 mm in length, stigma; club shaped, 155A in color, style; average of 2 mm in length, 155A in color, ovary; 146A in color.

*Stamens.*—2, anthers; average of 2 mm in length, dorsifixed, sessile (no filament) and implanted into inner side of tube, N77C in color, filaments; none, pollen; moderate in quantity and 4B in color.

*Fruit and seed.*—No seed or fruit produced to date.

It is claimed:

1. A new and distinct cultivar of *Syringa* plant named 'Annys200809' as herein illustrated and described.

* * * * *